(12) United States Patent
Efremova et al.

(10) Patent No.: US 7,725,992 B2
(45) Date of Patent: Jun. 1, 2010

(54) MECHANICAL FASTENER

(75) Inventors: Nadezhda V. Efremova, Neenah, WI (US); Garry Roland Woltman, Appleton, WI (US); Mary L. McDaniel, Appleton, WI (US); Roger Bradshaw Quincy, III, Cumming, GA (US); Nicholas Kraft, Appleton, WI (US); Thomas A. Eby, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 647 days.

(21) Appl. No.: 11/648,700

(22) Filed: Dec. 29, 2006

(65) Prior Publication Data

US 2008/0155798 A1    Jul. 3, 2008

(51) Int. Cl.
A44B 18/00 (2006.01)
A61F 13/15 (2006.01)

(52) U.S. Cl. .................................................... 24/442
(58) Field of Classification Search ........................ None
See application file for complete search history.

(56) References Cited

U.S. PATENT DOCUMENTS

| | | | |
|---|---|---|---|
| 4,794,028 A | 12/1988 | Fischer | |
| 5,260,015 A | 11/1993 | Kennedy et al. | |
| 6,059,764 A | 5/2000 | Osborn, III et al. | |
| 6,123,996 A | 9/2000 | Larsson et al. | |
| 6,149,934 A | 11/2000 | Krzysik et al. | |
| 6,180,205 B1 * | 1/2001 | Tachauer et al. | 428/100 |
| 6,248,880 B1 | 6/2001 | Karlson | |
| 6,323,389 B1 | 11/2001 | Thomas et al. | |
| 6,565,768 B1 | 5/2003 | Dentler et al. | |
| 6,588,073 B1 * | 7/2003 | Zoromski et al. | 24/446 |
| 6,639,066 B2 | 10/2003 | Boström et al. | |
| 2004/0102745 A1 * | 5/2004 | Linker et al. | 604/356 |
| 2004/0186448 A1 | 9/2004 | Misek et al. | |
| 2004/0258902 A1 | 12/2004 | Seth et al. | |
| 2005/0097713 A1 | 5/2005 | Ausen et al. | |
| 2005/0241119 A1 | 11/2005 | Efremova et al. | |
| 2005/0256477 A1 | 11/2005 | Van Gompel et al. | |
| 2006/0090307 A1 | 5/2006 | McDaniel et al. | |
| 2006/0142722 A1 | 6/2006 | Koenig et al. | |

FOREIGN PATENT DOCUMENTS

| | | |
|---|---|---|
| EP | 1656848 A | 5/2006 |
| WO | WO 0235956 A | 5/2002 |

OTHER PUBLICATIONS

PCT Search Report and Written Opinion for International Application No. PCT/IB2007/054717, dated Apr. 10, 2008.
Article—R.W. Unwin & Co. Ltd. 1993 *Metolose, Water- Soluble Cellulose Ethers* Shin+Etsu pp. 1-12.

* cited by examiner

*Primary Examiner*—Robert J Sandy
(74) *Attorney, Agent, or Firm*—Dority & Manning, P.A.

(57) ABSTRACT

A mechanical fastener is disclosed. The mechanical fastener generally comprises the male component of a hook and loop fastening system. The male component contains a plurality of protrusions that have been surface modified. In particular, the protrusions have been surfaced modified in a manner that prevents damage to a female component during engagement and disengagement but yet still forms a firm attachment with the female component.

26 Claims, 4 Drawing Sheets

MECHANICAL FASTENER

BACKGROUND

Disposable absorbent products, such as diapers, training pants, adult incontinence products, feminine hygiene products, and the like typically include some type of fastening system in order to fasten parts of the product together or to attach the product to the clothes of a wearer. In the past, various fastening systems on disposable absorbent products have been proposed including pins, ties, buttons, snaps, adhesives, and mechanical fastening systems.

For example, adhesives, such as pressure sensitive adhesives, have been used on diapers in order to attach the back of a diaper to the front of the diaper. Such adhesives have also been used on feminine hygiene products, such as absorbent pads, in order to attach the product to the wearer's underwear in order to maintain the product in a particular position. The use of adhesives, however, has various disadvantages and drawbacks. Adhesive-based fastening systems, for instance, may leave residue on the wearer's clothes, may stick to the wearer's hair and skin, can be moisture sensitive, and can be difficult to reposition without losing adhesive strength and other characteristics. Adhesives can also cause the products to stick to themselves and/or to other adjacent products.

In view of the above drawbacks, refastenable mechanical fastening systems such as hook and loop mechanical fastening systems have also been used on disposable absorbent products. Such fastening systems include a male component that is configured to engage a female component. The male component typically includes a backing material with a number of protruding hook elements. In conventional hook and loop fastening systems, the female component comprises a backing member having a plurality of loops that are engaged by the hook elements. For example, in one embodiment, the hook elements may include a base, a shank, and an engaging means in the form of a hook, a cap, a spherical/hemispherical shape, a flat top, etc.

Recently, microprotrusions have been used as the male component of a hook and loop mechanical fastening system. The microprotrusions, for instance, have a length of less than about 0.9 cm, such as from about 0.1 cm to about 0.001 cm. Such microprotrusions are capable of engaging most textile materials, in addition to loop materials, without the need of a specially shaped engaging means located at the top of the protrusions.

Mechanical fastening systems including microprotrusions are particularly well suited for use in feminine hygiene products. Such protrusions, for instance, are capable of engaging a wearer's underwear for maintaining the product in proper position. The underwear becomes the female component in the mechanical fastening system. Unfortunately, however, some of these mechanical fasteners can damage the underwear through unwanted engagement. This damage can take the form of abrasion, fiber put out, pilling, or snagging. Even when a single engagement of a component of the mechanical fastener system might produce minimal damage in the female component of the mechanical fastener system, multiple engagement of the male component of the mechanical fastener system might produce significant damage in the female component of the mechanical fastener system. This multiple engagement damage is especially important when one of the components is a durable (not disposable)—like underwear and the other component is disposable—like a feminine hygiene product.

There is currently a need to optimize engagement or maximize engagement with minimal system damage especially during multiple engagement usage when one component of the system is not disposable. One form would be a male component of a mechanical fastener that is not only capable of engaging a female component, but also minimizes damage to the female component during use of the mechanical fastening systems.

SUMMARY

In general, the present disclosure is directed to the male component of a mechanical fastening system, such as a hook and loop fastener. The male component comprises protrusions, such as microprotrusions, wherein at least a portion of the protrusions have been surface modified in amount sufficient to reduce female component damage like abrasion or fiber pull out caused by the protrusions. In other words, the surface modification of the protrusions prevents the protrusions from damaging an adjacent surface to which the mechanical fastener is attached. The mechanical fastener, for instance, is well suited to being used on an absorbent article such as a diaper, a training pant, a feminine hygiene product, an incontinence product, a wound care product, a medical garment, and the like. When used in a feminine hygiene product, for instance, the mechanical fastener is capable of holding the product in position by attaching a user's clothing without damaging the clothing during single or multiple engagements of the mechanical fastener system.

According to the present disclosure, the protrusions can be modified using various techniques. The technique can change the composition, the physical characteristics, and/or the structure of the surface of the protrusion. For instance, in one embodiment, an attachment modifying composition can be used to coat the protrusions. In an alternative embodiment, an attachment modifying composition may be blended with the polymeric material used to form the protrusions. In still another embodiment, the protrusions may be subjected to a heat treatment. For instance, the protrusions may be heated to a temperature greater than the glass transition temperature of the polymeric material used to form the protrusions. In one embodiment, a plurality of processes and techniques can be used to modify the protrusions. For instance, an attachment modifying composition can be used in conjunction with a heat treatment process to modify the protrusions.

Depending upon the technique or process used to modify the protrusions, the way in which the protrusions are modified can vary. The modification, for instance, to the protrusions may be chemical and/or physical. For instance, in one embodiment, the modification may cause structural changes in the protrusions. For instance, the shape of the protrusions may be altered. In one particular embodiment, the modification causes any edges present on the protrusions to become more rounded. In an alternative embodiment, the modification may change the overall shape of the protrusions. For example, the protrusions may be altered, causing the protrusions to be smoother and have a more rounded shape. After modification, for instance, the protrusions can have a circular or ovular cross-sectional shape.

In another embodiment, the modification to the protrusions may cause a change in the plasticity of the protrusions. The change in plasticity of the protrusions, for example, may only occur at the surface of the protrusions or may occur over the entire cross section of the protrusions. For instance, in one embodiment, the yield stress of the protrusions may be lowered. In this embodiment, for instance, the protrusions may be more likely to deform plastically during engagement or disengagement with an adjacent surface, such as a female component. In this manner, the protrusions are less likely to damage the material to which the mechanical fastener is attached.

In another embodiment, the modification may lower the surface energy of the protrusions. For instance, the protrusions may become effectively lubricated and have a lower coefficient of friction. In this manner, due to the shape of the protrusions, the protrusions may still be configured to form a secure attachment with the female component. By lowering the surface energy and/or the coefficient of friction of the surface of the protrusions, on the other hand, the protrusions are less likely to damage the female component during disengagement.

In still another embodiment, the protrusions can be modified in a manner so that a portion of the protrusions may be configured to transfer to an adjacent surface during disengagement. The material that transfers to the female component can be, for instance, a lubricating material or the protrusions can be configured to break apart upon disengagement, especially when the protrusions are located on a disposable article that is only intended for a single use. The portion that transfers to the female component can be insignificantly small so as not to be noticed. Alternatively, the portion that is transferred to the female component may later be removed through, for instance, a laundering process.

According to the present disclosure, the protrusions can be modified according to any of the above described modes. In addition, the protrusions can be modified by a combination of the above effects. For instance, during the modification process, the shape of the protrusions may be altered while also changing the plasticity of the protrusions. In still another embodiment, for instance, the shape of the protrusions may be altered while also lowering the surface energy, or the coefficient of friction of the protrusions.

As described above, one manner of modifying the protrusions is to contact the protrusions with an attachment modifying composition. The attachment modifying composition used in the present disclosure can vary depending upon the particular application and desired results. For instance, the attachment modifying composition may comprise a polymer wax, glycerol, monostearate, sorbitan tristearate, a fatty acid ester, a surfactant, a fluoropolymer, a silicone, a polysaccharide, graphite, or mixtures thereof. Particular surfactants that may be used as the attachment modifying composition include quaternary ammonium-based surfactants, zwiterionic surfactants, and alkylpolyglycoside surfactants.

In one particular embodiment, the attachment modifying composition may be applied to the protrusions as a coating. The coating may comprise, for instance, a polymer wax. The polymer wax may be naturally derived such as carnauba, montan, and paraffin, or synthetically produced such as paraffin from the Fischer-Tropsch coal gasification process, an amide polymer, a polyethylene, a polypropylene, a polybutene, a polyester, an ethylene acrylic acid, a polytetrafluoroethylene, or mixtures thereof. The polymer wax may be used alone or in combination with a surfactant. The coating composition may also contain a viscosity modifier. One example of a viscosity modifier, for instance, comprises a polysaccharide such as a cellulose derivative.

The attachment modifying composition may be present on the protrusions in an amount from about 0.01% to about 20% by weight. When the attachment modifying composition is present as a coating, the coating can have a thickness of less than about 20 microns.

When the attachment modifying composition is blended with the polymeric material used to form the protrusions, the attachment modifying composition may comprise, for instance, a fluoropolymer or a silicone. When using a silicone, the silicone may transfer to an adjacent material when a mechanical fastener is attached to the material.

In another embodiment, when the attachment modifying composition is blended with the polymeric material used to form the protrusions, the composition may be configured to transfer to the surface of the protrusions for changing the chemical and/or physical properties of the protrusions. In one embodiment, for instance, an attachment modifying composition may be blended with the polymeric material used to form the protrusions. After the protrusions are formed, the protrusions may be subjected to a heat treatment which facilitates transfer of the attachment modifying composition to the surface.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
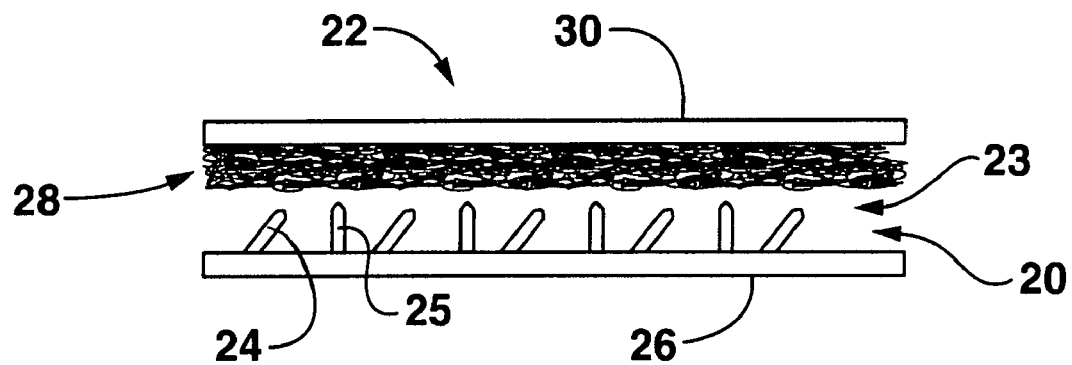
FIG. 1 is a side view of one embodiment of a mechanical fastening system that may be constructed in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

The present disclosure is generally directed to a mechanical fastening system that includes a male component that is capable of attaching to a female component. The male component of the mechanical fastening system may comprise hook elements of a hook and loop fastener system. The male component can be fastened to a variety of different materials serving as the female component and may remain securely fastened to the female component under effective levels of shear force. For instance, the female component may comprise any suitable fabric, such as a woven textile fabric, a knitted textile fabric, nonwoven materials, and the like.

More particularly, the present disclosure is directed to a male component of a mechanical fastening system that may be easily released or disengaged from the female component under the effective levels of shear force without causing noticeable damage or distortion to the female component. In one embodiment, the male component can be securely reattached if needed after several engagement-disengagement cycles. The male component includes a plurality of protrusions that have been surface modified. The surface modifications can reduce or eliminate damage to the female component, especially when the female component comprises a person's clothing.

In accordance with the present disclosure, the protrusions of the male component can be surface modified using various techniques. For instance, as will be described in greater detail below, in one embodiment, an attachment modifying composition can be applied to the protrusions. The attachment modifying composition, for instance, may be coated on the protrusions or may be blended with the polymeric material used to form the protrusions. In another embodiment, the protrusions can be subjected to a heat treatment that modifies the shape and geometry of the protrusions.

Modifying the surface of the protrusions can have various effects on the overall material. For instance, the surface modification can, in one embodiment, lower the surface energy of the protrusions. The surface modification can also cause a portion of the surface of the protrusions to deform plastically during engagement or disengagement with a female component. The attachment modifying composition or the heat treatment can also cause the edges of the protrusions to become smoother and more rounded or cause change in the composition of the surface due to blooming of different chemical compounds to the surface of the protrusions. In still another embodiment, an attachment modifying composition can be applied to the protrusions that serves as a lubricant between the protrusions and a female component. In fact, in one embodiment, the attachment modifying composition can be configured to transfer to the female component during engagement or disengagement.

The mechanical fastener of the present disclosure can be used in numerous applications. For instance, the mechanical fastener can be used with any suitable piece of clothing for attaching one portion to another portion. The mechanical fastener, for instance, can be used to attach any piece of one garment to another. In one embodiment, for instance, the mechanical fastener can be used on an absorbent article in order to position the article on a user. In one particular embodiment, for instance, the mechanical fastener can be used to secure a disposable absorbent article, such as an adult incontinence pad or a feminine care pad, to the wearer's undergarment.

In addition to articles of clothing, the mechanical fastener can also be used in various applications. For instance, the mechanical fastener can be used to attach name tags and visitor badges to garments. The mechanical fastener can also be used in toys and in fabric learning tools for children in order to attach and reattach items.

Referring to FIG. 1, one embodiment of a mechanical fastening system that can be modified in accordance with the present disclosure is shown. As illustrated, the mechanical fastening system includes a male component 20 and a female component 22. The male component 20 and the female component 22 may be brought together to be releasably attached or releasably engaged, to one another. The male component 20 may have a number of individual stems or protrusions 23 extending from a resilient backing material 26. In one embodiment, the protrusions 23 may be relatively small and may be considered microprotrusions.

The female component 22 may have a number of individual loops 28 protruding generally perpendicularly from a resilient loop backing material 30. The female component 22 may comprise any suitable material and may comprise a part or a component of a garment, such as a disposable absorbent article. The female component 22 may comprise, for instance, a knitted textile fabric, a woven textile fabric, a nonwoven textile fabric, or mixtures thereof.

The individual protrusions 23 of the male component 20 and the loops 28, such as individual fibers or bundles of fibers, of the female component 22, when brought into contact with one another, engage or interlock with one another. In particular, the protrusions 23 of the male component 20 latch on to the loops 28 of the female component 22 until forceably separated. For instance, when peeled apart, the protrusions 23 of the male component 20 are pulled out of the loops 28 of the female component 22.

As shown in FIG. 1, the male component 20 can include angled protrusions 24 and/or perpendicular protrusions 25. The manner in which the protrusions extend from the backing material 26 can be varied depending upon the particular application and desired result. Angled protrusions 24 as shown in FIG. 1, for instance, may also help to ensure that the female component 22 is not damaged during disengagement. For instance, angled protrusions are described and discussed in U.S. Patent Application Publication No. US2006/0090307 to McDaniel, et al., which is incorporated by reference.

When present, the angled protrusions 24 can form an angle with the backing material 26 in any suitable direction. In fact, in some embodiments, the orientation of the protrusions may be varied over the surface of the male component. When present, the protrusions 24 can form an angle with the backing material 26 of from about 5° to about 85°, such as about 15° to about 80°, such as about 20° to about 75° and, in one embodiment, from about 35° to about 70°. As shown in FIG. 1, the angled protrusions may be used alone or in conjunction with the perpendicular protrusions 25. In still other embodiments, the male component may be comprised entirely of the perpendicular protrusions 25.

When the protrusions 23 are formed, the protrusions may include edges that tend to contribute to increased interactions with the female component 22 creating pressure points at areas of high stress concentration during engagement and disengagement. These increased interactions can lead to increased engagement and snagging or other forms of damage to the female component. This phenomenon is especially problematic when the female component 22 comprises an article of clothing.

For instance, the female component can be damaged in various ways including but not limited to pilling, snagging, pull out, abrasion, distortion, wear, residue and the like. Pilling, for instance, is the tendency of woven fabrics and knits, especially wools, nylons, and acrylics, to form surface nubs or bunches of fibers. Pilling is caused by loosely twisted yarns and winding and interlocking with each other.

Fiber pull out is especially problematic. Fiber pull out is when the male component pulls on and releases fibers from the female component.

To reduce fiber pull out and possibly other sources of damage to the female component, the present disclosure is generally directed to modifying the protrusions 23. The manner in which the protrusions are modified can vary depending upon the particular application and the desired result. Of particular advantage, the protrusions can be modified according to the present disclosure so as to prevent damage to the female component without adversely interfering with the ability of the male component to engage the female component.

As described above, the protrusions on the male component can be modified using various techniques and methods. The modification to the protrusions, for instance, may be chemical and/or physical. For instance, in one embodiment, the protrusions may be modified by modifying the shape of the protrusions. For instance, the modification may cause any edges present on the protrusions to become more rounded. In another embodiment, the modification to the protrusions may cause a change in the plasticity of the protrusions. For instance, the yield stress of the protrusions may be lowered. The change in the plasticity of the protrusions may occur only over a portion of the protrusions or may occur over the entire protrusions. For instance, the change in plasticity may only occur at the surface of the protrusions. In still another embodiment, the protrusions are modified so as to lower the surface energy of the protrusions. For example, after being modified, the protrusions may have a lower coefficient of friction. In one embodiment, for instance, the surface of the protrusions may be lubricated so that the protrusions can easily disengage with the female component.

In still another embodiment, the protrusions may be modified so that a portion of the protrusions transfer to the female component during disengagement. During the transfer mode, for instance, portions of the protrusions may be configured to break apart and/or break off upon disengagement with the female component. In other words, the protrusions are modified so that the portions of the protrusions transfer to the female component instead of damaging the female component. The portions that are transferred to the female component can be, for instance, translucent, such as transparent so that they are not noticeable by the user. In one embodiment, any part of the protrusion that is transferred to the female component can be later released through cleaning or laundering of the female component. In another embodiment, the material that is transferred to the female component is so small that it is not noticeable by the user.

The portion of the protrusion that is transferred to the female component as described above may vary depending upon the particular application and the manner in which the protrusions are modified. For instance, in one embodiment, the protrusions substantially break apart during disengagement, especially when the male component is only to be used a single time. In an alternative embodiment, a lubricant may be present on the protrusions that is transferred to the female component. Examples, for instance, of lubricants that may transfer to an adjacent surface are disclosed in U.S. Patent Application Publication No. 2006/0142722 to Koenig, which is incorporated herein by reference.

After being processed according to the present disclosure, the chemical and/or physical characteristics of the protrusions may be modified according to a single mode or according to a combination of modes as described above. For instance, depending upon the technique used to modify the protrusions, any of the above described types of modifications may be combined. For instance, in one embodiment, not only is the shape of the protrusions modified, but also the lubricity of the protrusions may be modified. In still another embodiment, the protrusions may be modified so as to have a lower coefficient of friction and may also be modified so that a portion of the protrusions transfer to the female component during disengagement. It should be understood that any combination of modifications may occur according to the present disclosure. Further, the modifications to the protrusions may occur while also varying the type of backing material to which the protrusions are attached. For instance, in one embodiment, an extensible material may be used as the backing material in conjunction with the modified protrusions. Extensible backing materials, for instance, are disclosed in U.S. Pat. No. 6,059,764, which is incorporated herein by reference.

The above described modes of modification can be carried out on the protrusions using various different processes. For instance, in one embodiment, an attachment modifying composition can be used to coat the protrusions. In an alternative embodiment, an attachment modifying composition may be blended with the polymeric material used to form the protrusions. In still another embodiment, the protrusions may be subjected to a heat treatment. In still another embodiment, a plurality of processes and techniques can be used to modify the protrusions. For instance, an attachment modifying composition can be used in conjunction with the heat treatment process to modify the protrusions.

Figure 2:
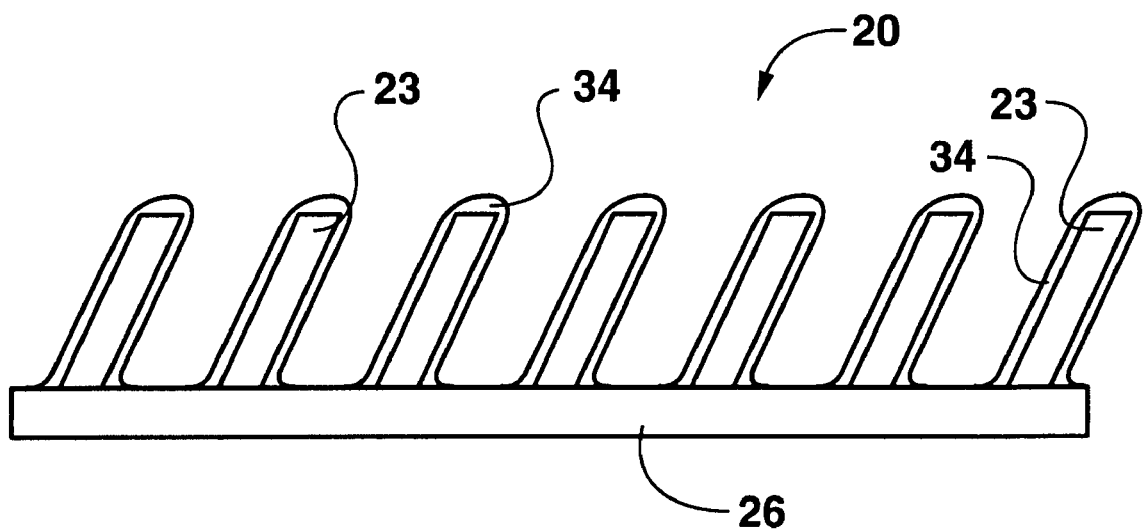
FIG. 2 is a side view of one embodiment of a mechanical fastener in accordance with the present disclosure.

Referring to FIG. 2, for instance, the male component 20 is illustrated in which the protrusions 23 include a coating 34 made from an attachment modifying composition. The coating can be present on all the protrusions or only on a portion of the protrusions. Further, the coating can cover the entire surface of each protrusion or may only cover a portion of the surface of each protrusion.

The attachment modifying composition used to form the coating 34 on the protrusions 23 can include various different ingredients depending upon the particular application. For instance, the attachment modifying composition may comprise a polymer wax, glycerol, monostearate, sorbitan tristearate, a fatty acid ester, one or more surfactants, a fluoropolymer, a silicone, a polysaccharide, graphite, or mixtures thereof. Particular surfactants that may be used include, for instance, a quaternary ammonium-based surfactant, a zwiterionic surfactant, or an alkylpolyglycoside surfactant.

In one embodiment, for instance, the attachment modifying composition may contain a polymer wax. In general, any suitable polymer wax may be used.

For instance, in one embodiment, the polymer wax may comprise an amide. The amide, for instance, may have the following chemical structure:

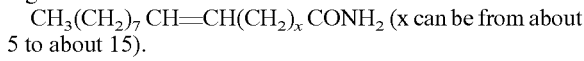

(x can be from about 5 to about 15).

Particular amide waxes that may be used include erucamide (also known as cis-13-docoscnoamide) having the formula:

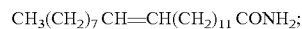

Oleylamide having the formula:

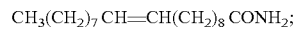

Oleamide having the formula:

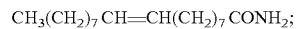

and mixtures thereof. Amide waxes are available from various commercial sources. For instance, such waxes are available as a water-based emulsion from Michelman, Inc. One particular wax available from Michelman, Inc. is Michem® Emulsion 27720 ("ME27720").

Other waxes that may be used to coat the protrusions include carnauba waxes, montan waxes, paraffin waxes, polyethylene waxes, polypropylene waxes, polybutene waxes, polyester waxes, ethylene acrylic acid waxes, polytetrafluoroethylene waxes, and mixtures thereof. One example of a polyolefin wax that may be used includes CATALLOY KS357 available from Montell.

In addition to polymer waxes, the attachment modifying composition may, in other embodiments, contain a polysaccharide and derivatives thereof (e.g., cellulosic ethers, gums, such as xanthan gum, etc.). Polysaccharides are polymers containing repeated carbohydrate units, which may be cationic, anionic, nonionic, and/or amphoteric. In one particular embodiment, for instance, the polysaccharide is a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the coating composition of the present invention are ethyl hydroxyethyl cellulose, methylethyl hydroxyethyl cellulose, methylethyl hydroxyethyl hydroxypropyl cellulose and methyl hydroxypropyl cellulose. In such embodiments, the hydroxyethyl groups typically constitute at least 30% of the total number of hydroxyalkyl groups, and the number of ethyl substituents typically constitutes at least 10% of the total number of alkyl substituents.

Particularly suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL." Further examples of suitable polysaccharides are described in more detail above.

In one particular embodiment, the polymer wax, such as an amide wax as described above, may be combined with a cellulose derivative to form a coating composition for coating the protrusions. For instance, in one embodiment, a water-based wax emulsion may be formulated containing from about 1% to about 25% by weight of a polymer wax and from about 0.5% to about 5% by weight of a cellulose derivative. For instance, in one particular embodiment, the coating composition may contain from about 2% to about 6% by weight of a polymer wax and about 1% by weight to about 3% by weight of a cellulose derivative.

In one embodiment, one or more surfactants can also be combined with a polymer wax and/or the modified cellulose in formulating the attachment modifying composition. In general, any suitable surfactant may be used. The surfactant may be added to the composition in order to better wet the surface of the protrusions and/or to improve the stability of the composition itself. In one embodiment, for instance, the surfactant may comprise a polymeric glucoside. Polymeric glucoside surfactants are commercially available, for instance, from the Cognis Corporation of Cincinnati, Ohio under the trade name GLUCOPON®. It should be understood however, that various other surfactants may be present.

In fact, in one embodiment, the protrusions on the male component can be coated with one or more surfactants only (absent the polymer wax or cellulose derivative). Suitable surfactants that may be used to coat the protrusions include, for instance, quaternary ammonium-based surfactants. Such surfactants are commercially available under the names INCROQUAT BENHENYLHE, CRODAZOSOFT DBQ, INCROMATE CDP, INCORMATE SDL, and CROSILKQUAT, which are all available from Croda, Inc.

In an alternative embodiment, one or more zwiterionic surfactants may be used to coat the protrusions. Zwiterionic surfactants have both anionic and cationic groups. Some examples of zwiterionic surfactants that may be used in the present disclosure include CROSULTAINE C-50 or CROSULTAINE B-30, which are both available from Croda, Inc.

Other materials that can be used in the attachment modifying composition in order to coat the protrusions include fatty acid esters, such as sorbitan esters. Examples of fatty acid esters include, for instance, sorbitan mono, di, or trioleate and their corresponding saturated stearate analogs. For instance, in one embodiment, sorbitan tristearate may be used. In another embodiment, glycerol monostearate may be used. Other components that may be present in the coating composition include fluoropolymers such as polytetrafluoroethylene. In addition, a silicone or graphite may be used to coat the protrusions. Any of the above components can be used alone or in combination with the other listed components.

Depending upon the ingredients contained in the attachment modifying composition, when applied as a coating, the composition can be applied to the male component using various application methods and techniques. For instance, the manner in which the attachment modifying composition is applied to the male component can depend upon the characteristics of the composition and various other factors. The composition can be applied to the male component using, for instance, various conventional coating techniques, such as by using a Meyer rod. Alternatively, the composition can be sprayed onto the male component, printed onto the male component or extruded onto the male component.

When applying a surfactant to the protrusions, the surfactant can be applied to the male component in multiple layers either by spraying or by dipping the material into the surfactant solution.

The amount of attachment modifying composition applied to the male component can also vary. In general, the composition can be coated onto the male component in an amount from about 0.05% to about 20% by weight, such as from about 0.5% to about 10% by weight. The thickness of the resulting coating can also vary. For instance, the thickness of the coating can be less than about 20 microns such as from about 1 micron to about 20 microns. The coating can be uniform over the surface of the protrusions or can be nonuniform. In fact, only a portion of the protrusions may be coated.

In order to increase the affinity of the attachment modifying composition to the surface of the protrusions, in one embodiment, the surface energy of the protrusions can be increased prior to the coating process. For instance, the protrusions can be pre-treated with oxygen plasma or corona treatment. Alternatively, surface-initiated plasma-polymerization can be used to chemically bind the coating composition to the surface of the protrusions.

In still another embodiment, atmospheric plasma may be used with, for example, silicone-based and/or fluorine-based precursors. During an atmospheric plasma process, an ionizing gas is created using an electrical gas discharge. Upon contact with the protrusions, the ionized gas causes surface chemical reactions. The gas can be controlled so that apolar moieties can be covalently attached to the surface of the protrusions. The apolar moieties may include, for instance, siloxane groups and/or perfluoroalkyl groups.

The coating compositions described above can modify the surface of the protrusions in various ways. For instance, in one embodiment, the coating composition can be used to lower the surface energy of the protrusions. Alternatively, the coating can be configured to deform plastically during engagement or disengagement with a female component. Still another embodiment, the coating composition can be configured to transfer to the female component during engagement and/or disengagement. In this manner, the coating composition can serve as a lubricant.

In still another embodiment, such as when using a polymer wax and/or a polysaccharide in the coating composition, the coating can be used to eliminate or reduce sharp edges on the protrusions. For instance, as shown in FIG. 2, the coating 34 gives the protrusions a more rounded shape especially over the cross-section of the protrusions.

In accordance with the present disclosure, the coating surface modification ultimately serves to reduce damage to the female component during engagement or disengagement without significantly adversely affecting the ability of the male component to attach to the female component. During engagement or disengagement the male component rubs or scrapes the female component causing the female component to abrade. Of particular advantage, the attachment modifying composition surface modification has been found to significantly reduce the abrasion to the female component.

The reduction in the abrasiveness of the male component is determined by a reduction in the abrasion damage done to the female component. This abrasion damage can be determined by many different methods. One suitable method is a modified ASTM D 4966-98 Standard Test Method for the Abrasion Resistance of Textile Fabrics (Martindale Abrasion Tester Method). This method and the operational manual for a Martindale Abrasion Tester are incorporated herein by reference. The method has been modified in the following way: (1) the male component will replace the standard abradant fabric within the method and (2) a suitable apparel fabric will replace the test specimen. A suitable apparel fabric would be a fabric that the male component would abrade in actual use. If the male component is part of a sanitary napkin, then the female component would be a fabric from underwear like Hanes Her Way TM Cotton Brief RN 15763 or its equivalent.

In addition to coating the protrusions, in an alternative embodiment, the attachment modifying composition can be blended with the material that is used to form the protrusions. For instance, the protrusions can be made from a thermoplastic polymer such as a polyamide, a polyester, a polyolefin such as polypropylene or polyethylene, or a blend of such polymers. In this embodiment, the attachment modifying composition can be blended with the polymer material used to form the protrusions either prior to or during the protrusion forming process. The attachment modifying composition in this manner can reduce friction, tack, electrostatic cling, or other properties of the protrusions. By decreasing the surface forces between the male component and the female component, the force that is exerted on the female component during disengagement may be decreased in amounts sufficient to prevent the female component from becoming damaged.

When blended with the polymer used to form the protrusions, the attachment modifying composition may also cause other modifications to occur. For instance, blending an attachment modifying composition with the polymer material used to form the protrusions can cause the shape of the protrusions to change or can change the plasticity characteristics of the protrusions. The attachment modifying composition may also cause the protrusions to break apart and transfer to a female component during disengagement.

When blending the attachment modifying composition with the polymer material used to form the protrusions, the attachment modifying composition can generally comprise any of the materials described above. In one embodiment, for instance, the attachment modifying composition may contain an ingredient that produces a surface bloom when blended with the polymer material and formed into the protrusions. Surface blooming refers to a process wherein a substance is added to a material and migrates from one region of the material to another region, particularly to a surface region. By migrating to the surface, the attachment modifying composition is capable of controlling the forces that are exerted on the female component when disengaged from the male component.

Particular examples of materials that may be blended with the polymer used to form the protrusions include one or more fluoropolymers, such as a fluorinated carbon compound. One example of a fluoropolymer that may be used is TEFLON polytetrafluoroethylene commercially available from DuPont. Other fluorinated thermoplastic polymers can also be used including FEP, PVDF and EFEP which are available from DuPont, Daikin Industries, and Atofina.

In another embodiment, the polymer used to form the protrusions may be blended with a silicone. Silicones, for instance, are known to migrate to the surface of a polymer object when blended with the polymer. For instance, in one particular embodiment, an organosilicone can be used, such as SILQUEST PA-1, which is commercially available from OSI. Other silicones that may be used can be obtained from Dow Corning. For instance, Dow Corning MB50-001 contains 50% by weight silicone and 50% by weight polypropylene precompounded together. Dow Corning MB50-002, on the other hand, contains 50% silicone and 50% polyethylene in a precompounded form.

When blended with the polymer material used to form the protrusions, the attachment modifying composition may be present in the protrusions in an amount from about 0.1% to about 90% by weight depending upon the particular application and the particular formulation. More particularly, the attachment modifying composition may be present in an amount from about 0.5% to about 50% by weight, such as from about 1% to about 5% by weight.

Figure 3:
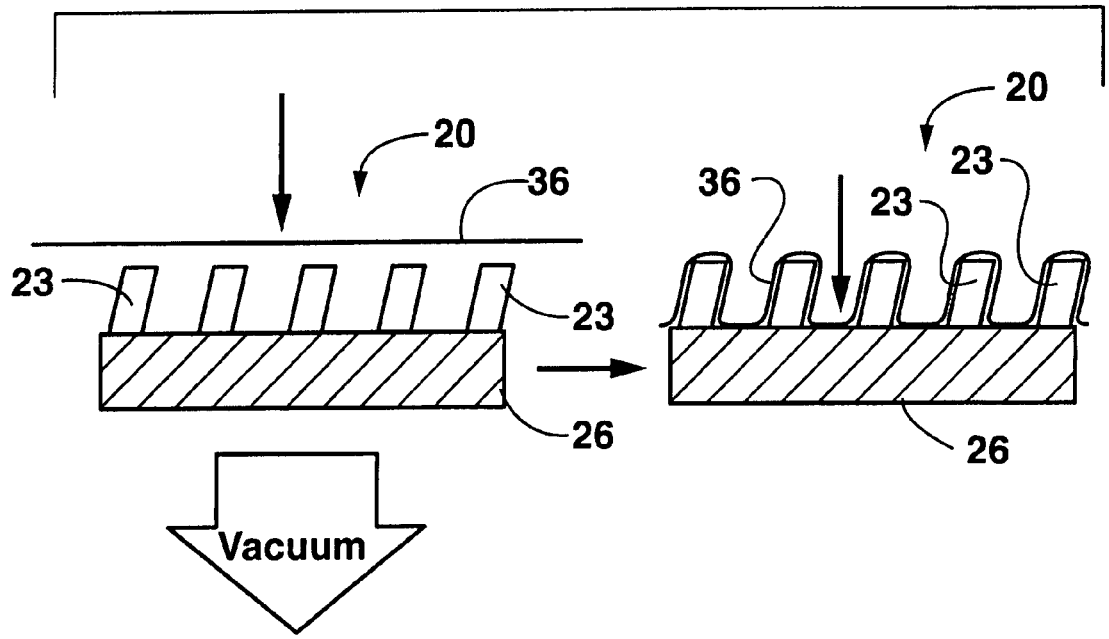
FIG. 3 is a side view of one embodiment of a process for constructing a mechanical fastener in accordance with the present disclosure.

Referring to FIG. 3, in another alternative embodiment of the present disclosure, the protrusions 23 of the male component 20 can be coated by a film 36. For instance, in one embodiment, as shown in FIG. 3, a relatively thin film 36 can be placed over the male component 20. Heat and optionally a vacuum can be applied to the male component causing the film to coat the protrusions 23 as shown. Once coated on the protrusions, the film can reduce sharp edges on the protrusions and make the protrusions more rounded. For instance, the film can potentially stretch at the edges of the protrusions becoming thinner by maintaining a greater thickness at the sides thus creating a more rounded and smoothed shape.

In addition to or instead of changing the shape of the protrusions, the film can also act as a lubricant on the protrusions. Alternatively, the film may change the plasticity characteristics of the protrusions or may be configured to transfer to a female component during disengagement.

In general, any suitable thermoplastic film may be used to coat the protrusions. The film, for instance, can be made from a polyolefin such as polyethylene or polypropylene, a polyester, or other similar polymer.

In still another embodiment, the protrusions 23 of the male component 20 can be subjected to a heat treatment for modifying the surface of the protrusions. For instance, the protrusions can be heated to a temperature above the glass transition temperature of the polymer used to form the protrusions. For instance, the protrusions can be heated to a temperature of from about 1° C. to about 10° C. above the glass transition temperature of the polymer. The protrusions can be heated for a sufficient amount of time so as to cause the edges of the protrusions to flow into a smoother configuration.

Figure 4A:
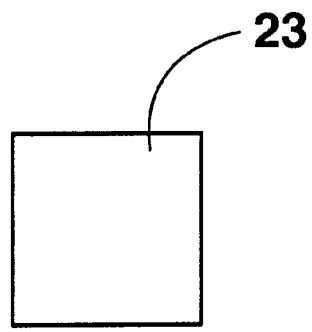
FIGS. 4A, 4B, and 4C are cross-sectional views of a protrusion as the protrusion is being heat treated in accordance with the present disclosure.
Figure 4B:
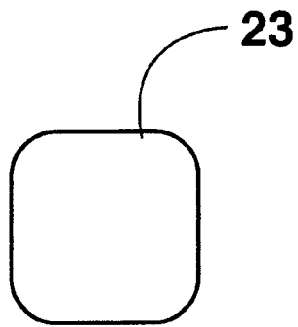
Figure 4C:
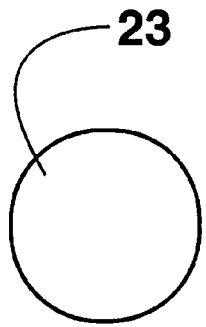
Figure 5:
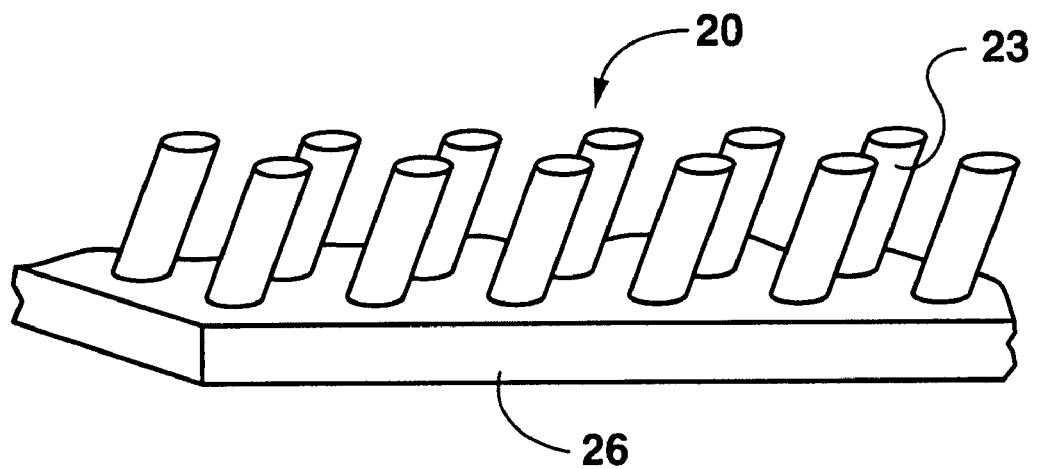
FIG. 5 is another embodiment of a mechanical fastener made in accordance with the present disclosure.

For instance, a protrusion 23 can have a cross-sectional shape as shown in FIG. 4A. After heat treatment as described above, the edges of the protrusions may begin flow to create a more rounded shape as shown in FIG. 4B. If desired, heating can be continued until a round or ovular shape is reached as shown in FIG. 4C. If desired, for instance, the protrusions 23 can have a cylindrical shape as shown in FIG. 5 after heat treatment.

Heat treating the protrusions may cause other changes to the protrusions in addition to or instead of changing the shape of the protrusions. For instance, in one embodiment, heat treatment may cause a particular material or component contained in the protrusions to migrate to the surface. For instance, heat treatment may be used in conjunction with an attachment modifying composition that has been blended with the polymeric material used to form the protrusions. Causing a material to migrate to the surface of the protrusions can have various effects. For instance, the material transferred to the surface may serve as a lubricant, may change the plasticity characteristics of the protrusions, and/or may be configured to transfer to a female component during disengagement.

After surface modification in accordance with the present disclosure, the protrusions 23 can have a variety of sizes and shapes. Overall, the protrusions may have tapered ends, may be conical, pyramidal, or cylindrical.

In one embodiment, the protrusions may comprise microprotrusions having a relatively small height. For instance, the height of the protrusions may be less than about 5 mm. For instance, the height may be from about 0.003 cm to about 0.9 cm, such as from about 0.02 cm to about 0.5 cm.

The protrusions may have a variety of cross-sectional dimensions. Further, the cross-sectional dimensions may change over the height of the protrusions. In general, the cross-sectional dimensions of the protrusions may range from about 90 microns to about 500 microns, such as from about 130 microns to about 440 microns.

The density of the protrusions can also vary depending upon the particular application. The male component, for instance, may have between about 16 and about 930 protrusions per square centimeter such as from about 124 to about 470 protrusions per square centimeter. In other embodiments, the density of the protrusions may be from about 250 to about 800 protrusions per square centimeter, such as from about 350 to about 700 protrusions per square centimeter.

The protrusions may be formed by injection molding, cavity molding, profile extrusion, or any other suitable fabricating process known in the art. For example, the protrusions may be suitably molded or extruded using a continuous molding process, in which a plastic resin strip base is molded with integral fastener elements in the form of protrusions extending from one surface. Such molding may be performed in a high pressure nip, such as between two counter-rotating rollers or against a single roller that defines miniature cavities in its peripheral surface.

The materials for making the protrusions may vary. As described above, the protrusions are generally made from one or more thermoplastic polymers. Such polymers include polyamides, polyesters, poly(vinyl acetate), PVC, polyolefins such as polyethylene or polypropylene, a thermoplastic elastomer, or mixtures thereof.

The Flexural Modulus of the material from which the protrusions are made can generally range from about 300 MPa to about 3000 MPa.

The backing material 26 (FIG. 5) of the male component can also be made from any suitable material. The backing material, for instance, may be made from the same or from a different material than the protrusions. The backing material may generally have a thickness in a range of from about 0.1 mm to about 5 mm. The backing material may comprise a film, a paper, a knit fabric, a woven fabric, a needle punched nonwoven fabric, a spunbond web, a neck bonded laminate, and the like.

The protrusions of the male component can be arranged on the backing material in any suitable geometry. For instance, the protrusions can be arranged in rows with spacers between the rows.

Figure 6:
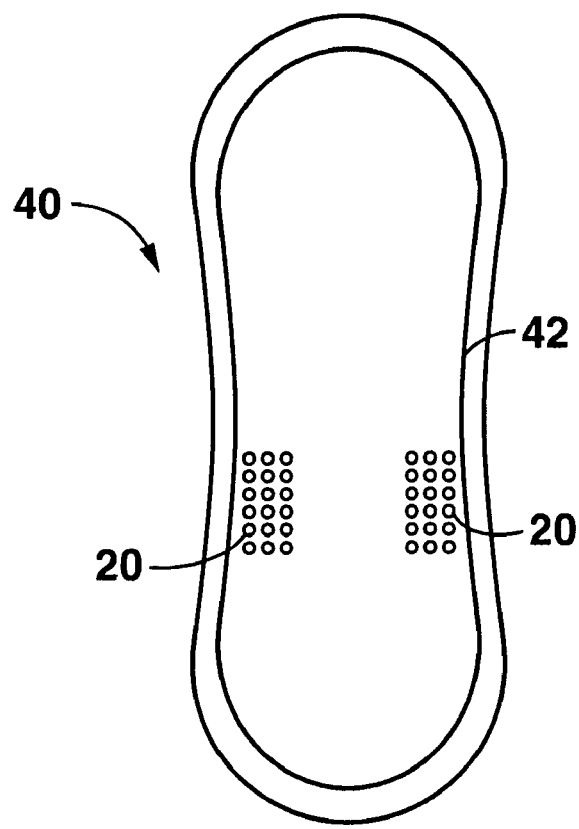
FIG. 6 is a plan view of a feminine hygiene product made in accordance with the present disclosure.

As described above, the mechanical fastener of the present disclosure can be used in numerous applications. In one particular application, for instance, as shown in FIG. 6, the male component 20 can be used on a feminine hygiene product 40. The feminine hygiene product 40 can include an outer cover material 42 opposite a liner. An absorbent core or material may be positioned in between the outer cover 42 and the liner. In accordance with the present disclosure, the male component 20 can be present on the outer cover for attaching the feminine hygiene product 40 to a person's undergarment. As described above, the protrusions that comprise the male component 20 are configured to prevent damage to the undergarment while still providing sufficient interlocking capability.

In general, any suitable feminine hygiene product may be used in accordance with the present disclosure. Other feminine hygiene products, for instance, are disclosed in U.S. Patent Application Publication No. US 2004/0186448 to Misek, which is incorporated herein by reference.

Figure 7:
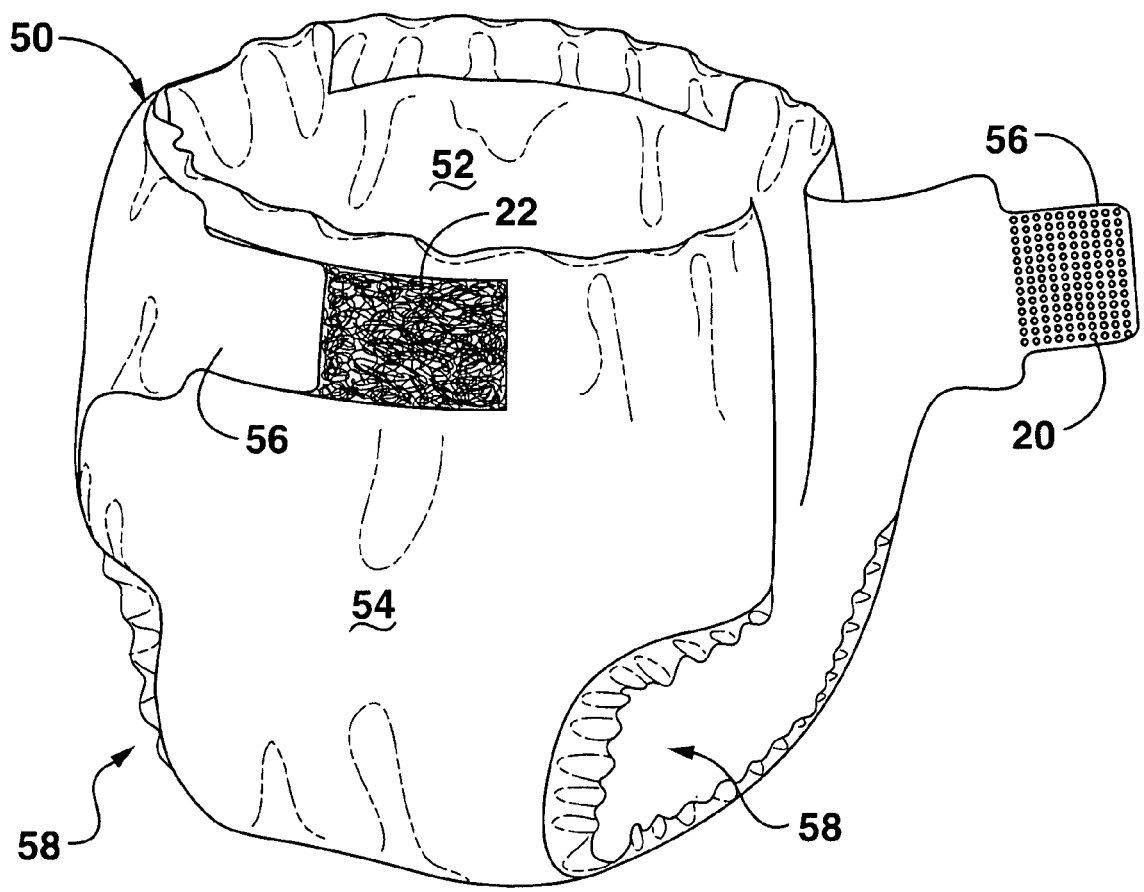
FIG. 7 is a perspective view of one embodiment of an absorbent article made in accordance with the present disclosure.

In still another embodiment, the male component 20 can be used on other absorbent articles such as a diaper 50 as shown in FIG. 7. The diaper 50 includes an outer cover 54, a liner 52, and an absorbent material positioned in between the outer cover and the liner. The diaper 50 further includes flaps 56 that are configured to attach the front portion of the diaper to the back portion so as to form leg openings 58. In accordance with the present disclosure, the flaps 56 can include the male component 20 made in accordance with the present disclosure. The male component 20 is configured to attach to a female component 22.

The present disclosure may be understood with reference to the following examples.

EXAMPLE 1

An attachment modifying composition was demonstrated. In a 250 milliliter PYREX® beaker, 124.7 grams of distilled water was heated to 69° C. Then, 2.5 grams of methylcellulose (Metolose SM-100, Shin-Etsu Chemical Co.) were added while stirring the warm water. Stirring was continued as the mixture was left to cool to room temperature. Next, 30.4 grams of Michem® Emulsion 27720 (synthetic amide wax type, 20% solids, from Michelman, Inc.) were added to the stirring formulation, and it was then cooled with an ice bath to 13° C. to generate viscosity. After the methylcellulose+ME27720/water formulation had warmed to room temperature, the viscosity was measured at 146 centipoise using a Brookfield DV-1 viscometer with an LV-3 spindle set at 100 rpm. Also, the percent solids of the formulation were measured at 5.40% using a Sartorius MA30 moisture analyzer. The calculated concentration of each component of the aqueous formulation is set forth below in Table 1.

TABLE 1

Components of the Aqueous Formulation

| Component | Calculated Amount |
|---|---|
| Michem ® Emulsion 27720 (solids) | 3.8% |
| Methylcellulose | 1.6% |
| Water | 94.6% |

The aqueous formulation was applied to the microprotrusion material using a #60 single wound coating rod. The coated pieces were placed in a laboratory oven at 80° C. for about 30 minutes to dry. The dried methylcellulose+ME27720 coating appeared to be uniform and attached to the microprotrusion material. The concentration of the components of the coating composition was calculated from the coated and dried pieces (1.92±0.08 grams), the untreated pieces (1.74±0.07 grams), and the composition of the aqueous formulation. The results are set forth below in Table 2.

TABLE 2

Components of the Coating Composition

| Component | Calculated Amount |
|---|---|
| Michem ® Emulsion 27720 (solids) | 70.4% |
| Methylcellulose | 29.6% |
| Solids Add-On Level | ~10.5% |

EXAMPLE 2

An attachment modifying composition was demonstrated. In a 400 milliliter PYREX® beaker, 196.0 grams of distilled water was heated to 70° C. Then, 4.0 grams of methylcellulose (Metolose SM-400, Shin-Etsu Chemical Co.) were added while stirring the warm water. Stirring was continued as the mixture was left to cool to about 27° C. Next, 49.6 grams of Michem® Emulsion 27720 (synthetic amide wax type, 20% solids, from Michelman, Inc.) were added to the stirring formulation, and after about 30 minutes, it was then cooled with an ice bath to 14° C. to generate viscosity. After the methylcellulose+ME27720/water formulation had warmed to room temperature, the viscosity was measured at 397 centipoise using a Brookfield DV-1 viscometer with an LV-3 spindle set at 100 rpm. Also, the percent solids of the formulation were measured at 5.01% using a Sartorius MA30 moisture analyzer. The calculated concentration of each component of the aqueous formulation is set forth below in Table 3.

TABLE 3

Components of the Aqueous Formulation

| Component | Calculated Amount |
|---|---|
| Michem ® Emulsion 27720 (solids) | 4.0% |
| Methylcellulose | 1.6% |
| Water | 94.4% |

The aqueous formulation was applied to the microprotrusion material using a #60 single wound coating rod. The coated pieces (3 inches by 10.5 inches) were placed in a laboratory oven at 80° C. for about 30 minutes to dry. The dried methylcellulose+ME27720 coating appeared to be uniform and attached to the microprotrusion material. The concentration of the components of the coating composition was calculated from the coated and dried pieces (2.14±0.02 grams), the untreated pieces (1.91±0.02 grams), and the composition of the aqueous formulation. The results are set forth below in Table 4.

TABLE 4

Components of the Coating Composition

| Component | Calculated Amount |
|---|---|
| Michem ® Emulsion 27720 (solids) | 71.4% |
| Methylcellulose | 28.6% |
| Solids Add-On Level | ~12.3% |

EXAMPLE 3

An attachment modifying composition was demonstrated. In a 400 milliliter PYREX® beaker, 196.0 grams of distilled water was heated to 68° C. Then, 4.0 grams of methylcellulose (Metolose SM-400, Shin-Etsu Chemical Co.) were added while stirring the warm water. Stirring was continued as the mixture was left to cool to room temperature. Then, the surface tension and viscosity were measured for the methylcellulose/water formulation. For the surface tension measurement, distilled water was measured first by placing 80 milliliters in a 100 milliliter PYREX® beaker. A value of 74 dynes/cm was obtained by using a Krüss Processor Tensiometer K12 with the plate method. Next, the distilled water was discarded from the beaker and replaced with about 80 milliliters of the methylcellulose/water formulation. The surface tension of the formulation was measured at 53 dynes/cm. For the viscosity measurement, a Brookfield DV-1 viscometer with an LV-3 spindle set at 100 rpm was used to obtain a value of 539 centipoise.

The methylcellulose/water formulation was used to coat the microprotrusion material using a #60 single wound coating rod. However, the coating was not uniform on the substrate, most likely due to the high surface tension of the formulation. Therefore, a surfactant was added to the methylcellulose/water formulation. In a 250 milliliter PYREX® beaker, 0.86 gram of Glucopon® 220 UP (alkyl polyglycoside, 60% active, from Cognis Corporation) was added to 171.0 grams of the methylcellulose/water formulation. After stirring for about 1.5 hours, the surface tension and viscosity were measured at 30 dyne/cm and 431 centipoise, respectively, using the same procedures described above. Therefore, the surfactant was effective at reducing the surface tension of the formulation. The calculated concentration of each component of the aqueous formulation is set forth below in Table 5.

TABLE 5

Components of the Aqueous Formulation

| Component | Calculated Amount |
|---|---|
| Glucopon ® 220 UP (solids) | 0.3% |
| Methylcellulose | 2.0% |
| Water | 97.7% |

The aqueous formulation was applied to the microprotrusion material using a #60 single wound coating rod. The coated pieces were placed in a laboratory oven at 80° C. for about 30 minutes to dry. The dried methylcellulose+Glucopon® coating was different from the methylcellulose+ ME27720 wax coatings described in Examples 1 and 2. For example, the methylcellulose+Glucopone coating appeared to be brittle and develop fractures, perhaps due to poor adhesion to the microprotrusion material. This was not seen with the methylcellulose+ME27720 wax coatings. The concentration of the components of the methylcellulose+Glucopon® coating composition was calculated from the coated and dried pieces (2.10±0.04 grams), the untreated pieces (1.99±0.04 grams), and the composition of the aqueous formulation. The results are set forth below in Table 6.

TABLE 6

Components of the Coating Composition

| Component | Calculated Amount |
|---|---|
| Glucopon ® 220 UP (solids) | 13.0% |
| Methylcellulose | 87.0% |
| Solids Add-On Level | ~5.8% |

EXAMPLE 4

The male component of a mechanical fastening system as produced in Example 2 above was tested for fiber pull out. In particular, a 2"×2" piece of the sample was manually engaged with a piece of nylon fabric by pulling the sample across the surface of the fabric. A small amount of pressure was applied to keep the protrusions engaging the fabric. The above motion was repeated four to five times in perpendicular directions.

After the male component was engaged with the nylon fabric, a one-half inch by one-half inch sample of the male component was cut in the center area to minimize any differences that may have occurred near the edges. The samples were then examined under a microscope and the fibers entrapped in the protrusions were counted. Four different samples of the male component were tested. In addition, a similar uncoated male component was also similarly tested and used as a control. The following results were obtained:

TABLE 1

Fiber Pull Out Analysis
Fiber Pull Out

| Test Run No. | Uncoated | Coated |
|---|---|---|
| 1 | 130 | 25 |
| 2 | 58 | 23 |
| 3 | 61 | 13 |
| 4 | 33 | 10 |

TABLE 1-continued

As shown above, the male component coated in accordance with the present disclosure greatly reduced fiber pull out damage to the nylon material in comparison to similar uncoated samples. It was also observed that the coated samples increased in stiffness indicating that there may actually be an increase in engagement with a female component.

EXAMPLE 5

The male components produced in Example Nos. 1 and 2 above were also examined under scanning electron microscopy. From a visual observation, it was noticed that the coating layer was relatively thin but fairly uniform on the upper surface of the protrusions but tapered to a thinner layer close to the tip. The coating layer was thickest on the underside of the protrusions. The coating had a thickness of less than about 1 micron near the tip of the protrusions to about 25 microns near the base of the protrusions. The sides of the protrusions generally had a coating thickness of from about 2 microns to about 10 microns.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A mechanical fastener comprising:
   a backing material;
   a plurality of protrusions extending from the backing material, the protrusions being formed from a polymeric material;
   wherein each protrusion has an outer surface;
   wherein at least a portion of the outer surface of the protrusions have been modified in an amount sufficient to decrease surface forces between the outer surfaces of the protrusions and a corresponding material, that has not been modified, during engagement and disengagement between the protrusions and the material.

2. A mechanical fastener as defined in claim 1, wherein the outer surface of the protrusions have been modified by applying an attachment modifying composition to at least a portion of the outer surface of the protrusions.

3. A mechanical fastener as defined in claim 2, wherein the attachment modifying composition comprises a coating containing a polymer wax, a surfactant, a polysaccharide or mixtures thereof.

4. A mechanical fastener as defined in claim 2, wherein the attachment modifying composition comprises glycerol, monostearate, sorbitan tristearate, a fatty acid ester, a quaternary ammonium-based surfactant, a zwitterionic surfactant, a fluoropolymer, a silicone, a polysaccharide, an alkylpolyglycoside surfactant, graphite, or mixtures thereof.

5. A mechanical fastener as defined in claim 1, wherein at least a portion of the outer surface of the protrusions deformed plastically during engagement or disengagement.

6. A mechanical fastener as defined in claim 1, wherein the surface modification of the protrusions lowers the surface energy of the protrusions.

7. A mechanical fastener as defined in claim 1, wherein at least a portion of the surface modification of the protrusions transfers to an adjacent surface during engagement or disengagement with the surface.

8. A mechanical fastener as defined in claim 1, wherein the outer surface of the protrusions are modified by at least partially rounding at least one edge present on the cross-sectional shape of the protrusions.

9. A mechanical fastening system comprising:
a male component comprising the mechanical fastener defined in claim 1 and a female component capable of engaging the male component.

10. A mechanical fastening system as defined in claim 9, wherein the female component comprises a woven textile fabric, a knitted textile fabric, a nonwoven web, or combinations thereof 11. A mechanical fastener as defined in claim 1, wherein the protrusions have a height of less than about 5 mm.

12. A mechanical fastener as defined in claim 3, wherein the coating comprises the polymer wax, the polymer wax comprising an amide polymer.

13. A mechanical fastener as defined in claim 12, wherein the coating further comprises a viscosity modifier.

14. A mechanical fastener as defined in claim 13, wherein the viscosity modifier comprises a cellulose derivative.

15. A mechanical fastener as defined in claim 3, wherein the coating comprises the surfactant, the surfactant comprising a quaternary ammonium surfactant, a zwiterionic surfactant, or an alkylpolyglycoside.

16. A mechanical fastener as defined in claim 3, wherein the coating present on the surface of the protrusions has a thickness of less than about 20 microns.

17. A mechanical fastener as defined in claim 3, wherein the coating contains the polymer wax, the polymer wax comprising polyethylene, polypropylene, polyester, or mixtures thereof.

18. A mechanical fastener as defined in claim 3, wherein the coating contains the polymer wax combined with the surfactant.

19. An absorbent article comprising an outer cover, a liner, and an absorbent core positioned in between the outer cover and the liner, the mechanical fastener as defined in claim 1 being positioned on the outer cover.

20. An absorbent article as defined in claim 19, wherein the absorbent article comprises a feminine hygiene product.

21. A mechanical fastener as defined in claim 1, wherein the outer surface of the protrusions have been modified by blending the polymeric material used to form the plurality of protrusions with an attachment modifying composition.

22. A mechanical fastener as defined in claim 21, wherein the attachment modifying composition comprises a fluoropolymer, a polysaccharide, or a silicone.

23. A mechanical fastener as defined in claim 1, wherein the outer surface of the protrusions have been modified by exposing the protrusions to sufficient heat to cause at least one edge on the protrusions to become more rounded.

24. A mechanical fastener as defined in claim 23, wherein the polymeric material has a glass transition temperature and wherein the plurality of protrusions have been heated to a temperature greater than the glass transition temperature of the polymeric material.

25. A mechanical fastener as defined in claim 23, wherein at least certain of the protrusions have a circular or ovular cross-sectional shape after the heat treatment.

26. A mechanical fastener as defined in claim 1, wherein the outer surface of the protrusions have been modified by contacting the protrusions with an attachment modifying composition and then subjecting the protrusions to a heat treatment.

* * * * *